(12) United States Patent
Xu et al.

(10) Patent No.: US 9,165,338 B2
(45) Date of Patent: Oct. 20, 2015

(54) METHOD, DEVICE AND COMPUTER-READABLE STORAGE MEDIUM FOR PANORAMIC IMAGE COMPLETION

(71) Applicant: Tencent Technology (Shenzhen) Company Limited, Guangdong (CN)

(72) Inventors: Kun Xu, Guangdong (CN); Jianyu Wang, Guangdong (CN); Baoli Li, Guangdong (CN); Haifeng Deng, Guangdong (CN); Zhe Zhu, Guangdong (CN)

(73) Assignee: Tencent Technology (Shenzhen) Company Limited, Guangdong (CN)

( * ) Notice: Subject to any disclaimer, the term of this patent is extended or adjusted under 35 U.S.C. 154(b) by 0 days.

(21) Appl. No.: 14/449,674

(22) Filed: Aug. 1, 2014

(65) Prior Publication Data
US 2015/0170332 A1 Jun. 18, 2015

Related U.S. Application Data

(63) Continuation of application No. PCT/CN2013/089703, filed on Dec. 17, 2013.

(30) Foreign Application Priority Data

Jan. 18, 2013 (CN) .......................... 2013 1 0019530

(51) Int. Cl.
| | |
|---|---|
| G06T 3/00 | (2006.01) |
| H04N 5/341 | (2011.01) |
| A61B 6/02 | (2006.01) |
| G06T 5/00 | (2006.01) |
| H04N 5/232 | (2006.01) |
| H04N 13/00 | (2006.01) |
| G02B 13/06 | (2006.01) |
| G06T 3/40 | (2006.01) |

(52) U.S. Cl.
CPC ............... *G06T 3/0062* (2013.01); *A61B 6/025* (2013.01); *G06T 3/0087* (2013.01); *G06T 5/005* (2013.01);

(Continued)

(58) Field of Classification Search
CPC .................. G06T 3/0062; G06T 5/005; G06T 2207/20016; G06T 2200/32; G06T 3/0087; G06T 3/4038; H04N 5/23238; H04N 5/3415; H04N 2013/0088; A61B 6/025; G02B 13/06
See application file for complete search history.

(56) References Cited

U.S. PATENT DOCUMENTS

| | | | | |
|---|---|---|---|---|
| 4,566,763 | A | * | 1/1986 | Greguss ........................ 359/725 |
| 4,807,158 | A | * | 2/1989 | Blanton et al. ................ 345/581 |

(Continued)

FOREIGN PATENT DOCUMENTS

| | | |
|---|---|---|
| CN | 101196561 A | 6/2008 |
| CN | 101414379 A | 4/2009 |
| CN | 101482968 A | 7/2009 |

OTHER PUBLICATIONS

PCT International Search Report, dated Mar. 20, 2014; 9 pgs.

*Primary Examiner* — Manav Seth
(74) *Attorney, Agent, or Firm* — Seyfarth Shaw LLP (57) ABSTRACT

A method for panoramic image completion is disclosed. The method includes: acquiring a panoramic image; obtaining a projected image by mapping pixels of the panoramic image onto a polar coordinate system, wherein a long side component of the pixel coordinate of the pixels is corresponding to the polar angle of the polar coordinate system and a short side component of the pixel coordinate of the pixels is corresponding to a radial coordinate of the polar coordinate system; acquiring an incomplete region of the projected image, and obtaining a completed image by completing the incomplete region; and obtaining a completed panoramic image by inverse mapping the pixels of the completed image according to the polar coordinate system. Furthermore, a device for panoramic image completion is also disclosed. The above method and device for panoramic image completion take account of the perspective curvature of the panoramic image, to improve the degree of restoration.

18 Claims, 5 Drawing Sheets

(52) U.S. Cl.
CPC ......... *H04N 5/23238* (2013.01); *H04N 5/3415* (2013.01); *G02B 13/06* (2013.01); *G06T 3/4038* (2013.01); *G06T 2200/32* (2013.01); *G06T 2207/20016* (2013.01); *H04N 2013/0088* (2013.01)

(56) References Cited

U.S. PATENT DOCUMENTS

| | | | |
|---|---|---|---|
| 5,537,251 A * | 7/1996 | Shimada | 359/462 |
| 5,694,531 A * | 12/1997 | Golin et al. | 345/419 |
| 5,790,181 A * | 8/1998 | Chahl et al. | 348/36 |
| 5,960,108 A * | 9/1999 | Xiong | 382/154 |
| 5,963,213 A * | 10/1999 | Guedalia et al. | 345/427 |
| 5,963,664 A * | 10/1999 | Kumar et al. | 382/154 |
| 6,031,540 A * | 2/2000 | Golin et al. | 345/419 |
| 6,320,584 B1 | 11/2001 | Golin et al. | 345/629 |
| 6,389,179 B1 * | 5/2002 | Katayama et al. | 382/284 |
| 6,424,377 B1 * | 7/2002 | Driscoll et al. | 348/335 |
| 6,426,774 B1 * | 7/2002 | Driscoll et al. | 348/335 |
| 6,459,451 B2 * | 10/2002 | Driscoll, Jr. et al. | 348/335 |
| 6,683,608 B2 * | 1/2004 | Golin et al. | 345/419 |
| 7,042,508 B2 * | 5/2006 | Jan et al. | 348/335 |
| 7,123,777 B2 * | 10/2006 | Rondinelli et al. | 382/284 |

* cited by examiner

METHOD, DEVICE AND COMPUTER-READABLE STORAGE MEDIUM FOR PANORAMIC IMAGE COMPLETION

CROSS REFERENCE TO RELATED APPLICATION

This application is a continuation application of International Application No. PCT/CN2013/089703, filed Dec. 17, 2013, entitled "METHOD, DEVICE AND COMPUTER-READABLE STORAGE MEDIUM FOR PANORAMIC IMAGE COMPLETION" which claims priority to Chinese patent application No. CN 201310019530.6, filed Jan. 18, 2013. The above-referenced applications are hereby incorporated herein in their entireties by reference.

TECHNICAL FIELD

The present disclosure relates generally to the technological field of image processing, and more particularly, to a method, device and computer-readable storage medium for panoramic image completion.

BACKGROUND

A panoramic image is any wide-angle view or representation of a physical space, whether in drawing, painting, photography, film/video, or a three-dimensional model. The panoramic image can be a volume panoramic image or a 360-degree panoramic image. A panoramic image can be created by using a panoramic camera. For example, a graduation photo in volume panoramic view can be taken by the panoramic camera.

If a blurred phenomenon or pixel loss occurs in a region of a panoramic image, the panoramic image needs to be completed. For example, when fixing a scanned old panoramic photo, it is necessary to complete the blurred region on the old photo.

Conventionally, the method for normal image completion is used to complete a panoramic image. In the method, the completion is based on the values of the pixels in a region adjacent to the blurred or pixel loss region. However, because a sphere lens is usually used for wide-angle in creating a panoramic image, the completed panoramic image will appear serious distortion and stretching when using the conventional method to complete the panoramic image, which results in low degree of restoration of the panoramic image.

SUMMARY

According to an aspect of the disclosure, a method for panoramic image completion includes:
acquiring a panoramic image;
obtaining a projected image by mapping each pixel coordinate of the panoramic image onto a polar coordinate system, wherein a long side component of the pixel coordinate is corresponding to a polar angle of the polar coordinate system and a short side component of the pixel coordinate is corresponding to a radial coordinate of the polar coordinate system;
acquiring an incomplete region of the projected image, and obtaining a completed image by completing the incomplete region; and
obtaining a completed panoramic image by inverse mapping each pixel coordinate of the completed image according to the polar coordinate system.

According to a further aspect of the disclosure, a device for panoramic image completion includes:
an image acquisition module, configured to acquire a panoramic image;
an image mapping module, configured to obtain a projected image by mapping pixels of the panoramic image onto a polar coordinate system, wherein a long side component of each pixel coordinate is corresponding to a polar angle of the polar coordinate system and a short side component of the pixel coordinate is corresponding to a radial coordinate of the polar coordinate system;
an image completion module, configured to acquire an incomplete region of the projected image and obtain a completed image by completing the incomplete region; and
an image inverse mapping module, configured to obtain a completed panoramic image by inverse mapping each pixel coordinate of the completed image according to the polar coordinate system.

According to a further aspect of the disclosure, a non-transitory computer-readable storage medium comprising an executable program to execute a method for panoramic image completion, the method includes:
acquiring a panoramic image;
obtaining a projected image by mapping each pixel coordinate of the panoramic image onto a polar coordinate system, wherein a long side component of the pixel coordinate is corresponding to a polar angle of the polar coordinate system and a short side component of the pixel coordinate is corresponding to a radial coordinate of the polar coordinate system;
acquiring an incomplete region of the projected image, and obtaining a completed image by completing the incomplete region; and
obtaining a completed panoramic image by inverse mapping each pixel coordinate of the completed image according to the polar coordinate system.

In the above method and device for panoramic image completion, firstly map pixels of the panoramic image onto a polar coordinate system to obtain a projected image, then complete the projected image to obtain a completed image, finally inverse map the completed image to obtain a completed panoramic image. Because the angle of a panoramic image has a spherical curvature during photographing or generation, the method that obtaining a projected image by mapping pixels of the panoramic image onto a polar coordinate system then completing the projected image adequately takes account of the perspective curvature of the panoramic image, which avoids serious distortion and stretching in the completed panoramic image, and thus improve the degree of restoration.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE EMBODIMENTS

In the following description of embodiments, reference is made to the accompanying drawings which form a part hereof, and in which it is shown by way of illustration specific embodiments of the disclosure that can be practiced. It is to be understood that other embodiments can be used and structural changes can be made without departing from the scope of the disclosed embodiments.

Figure 1:
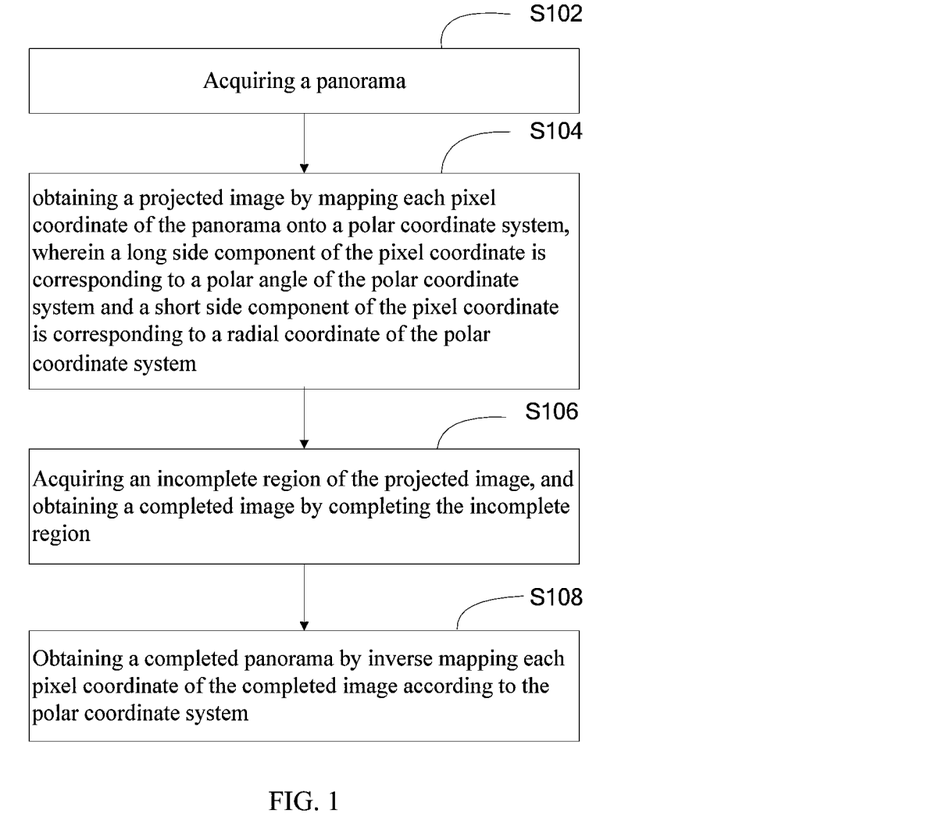
FIG. 1 is a schematic diagram illustrating a method for panoramic image completion according to one embodiment of the present disclosure.

In one embodiment of the present disclosure, as shown in FIG. 1, a method for panoramic image completion includes:

Step 102, acquiring a panoramic image.

Figure 2:
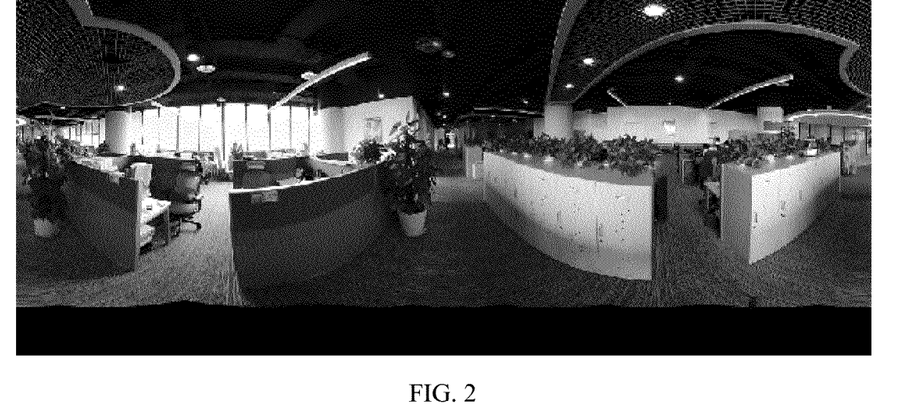
FIG. 2 is an explanatory image illustrating a panoramic image to be completed according to one embodiment of the present disclosure.

The panoramic image can be an image taken by a panoramic camera. The lens of the panoramic camera is usually a fisheye lens which is an ultra wide-angle spherical lens, rather than a flat lens used by an ordinary camera. As shown in FIG. 2, the panoramic angle of the panoramic image can be 360 degree, that is, an image created by making a complete cycle around a photographer.

Step S104, obtaining a projected image by mapping each pixel coordinate of the panoramic image onto a polar coordinate system, wherein a long side component of the pixel coordinate is corresponding to a polar angle of the polar coordinate system and a short side component of the pixel coordinate is corresponding to a radial coordinate of the polar coordinate system.

The long side component of the pixel coordinate of the pixels in the panoramic image is a component in the direction extending along the longer edge in the panoramic image, and the short side component of the pixel coordinate of the pixels in the panoramic image is a component in the direction extending along the shorter edge in the panoramic image, referring to FIG. 2.

It should be noted that a longitudinal panoramic image that is shown by longitudinal wide-angle in the visual orientation can be rotate 90 degree to be a transverse panoramic image before mapping.

In other words, by mapping the pixel coordinate in the panoramic image onto a polar coordinate system, obtaining the degree of the polar angle corresponding to the pixel in the polar coordinate system based on the long side component of the pixel, and obtaining the length of the radial coordinate corresponding to the pixel in the polar coordinate system based on the short side component of the pixel, a circular or sectorial (circular, when the panoramic angle is 360 degree) projected image can be finally obtained.

In one embodiment of the present disclosure, the step of obtaining a projected image by mapping the pixel coordinate of the pixel in the panoramic image onto a polar coordinate system may include:

calculating the corresponding polar angle based on the long side component of the pixel coordinate of the pixel in the panoramic image, and calculating the corresponding radial coordinate based on the short side component of the pixel coordinate of the pixel in the panoramic image; and creating a projected image by acquiring a projected pixel coordinate of the projected image corresponding to the pixel coordinate in the panoramic image, based on the polar angle and the radial coordinate.

In this embodiment, the polar angle and radial coordinate can be calculated by a formula of:

$$\begin{cases} \theta = 2\pi \times \frac{x_{Panorama}}{a \times \text{Width}} \\ \rho = b \times (\text{Height} - y_{Panorama}) \end{cases}$$

wherein $x_{Panorama}$ represents a long side component of the pixel coordinate of the pixel in the panoramic image, $y_{Panorama}$ represents the short side component of the pixel coordinate of the pixel in the panoramic image, $\theta$ represents the polar angle in the polar coordinate system corresponding to the panoramic image, $\rho$ represents the radial coordinate in the polar coordinate system corresponding to the panoramic image, Width represents the length of the long side of the panoramic image, Height represents the length of the short side of the panoramic image, a represents a panoramic angle ratio, and b represents a scale ratio.

Figure 3:
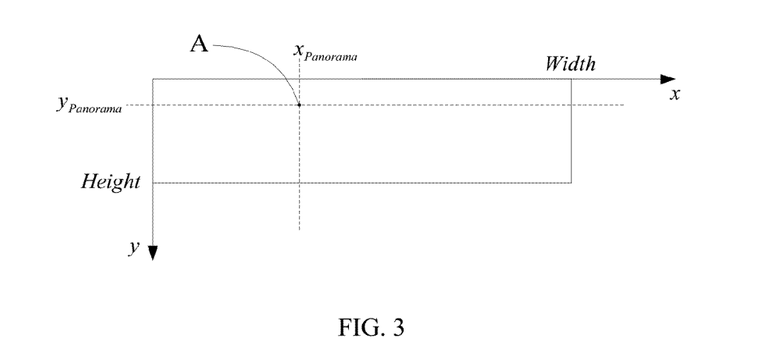
FIG. 3 is a schematic diagram illustrating the coordinate transformation of mapping the panoramic image onto a polar coordinate system to obtain a projected image according to one embodiment of the present disclosure.
Figure 4:
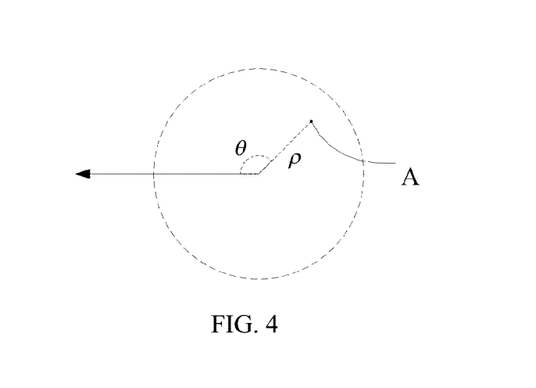
FIG. 4 is a schematic diagram illustrating the coordinate transformation of mapping the panoramic image onto a polar coordinate system to obtain a projected image according to one embodiment of the present disclosure.

For example, as shown in FIG. 3 and FIG. 4, if the panoramic angle ratio a is 1, namely, the panoramic angle of the panoramic image is 360 degree, and if the scale ratio b is 1, namely, the maximum length of the radial coordinate is Height.

In the embodiment, the pixel coordinate of the pixel in the projected image can be calculated by an formula of:

$$\begin{cases} x_{project} = \rho \times (1 + \cos\theta) \\ y_{project} = \rho \times (1 - \sin\theta) \end{cases}$$

wherein $x_{project}$ represents a horizontal component of the pixel coordinate of the pixel in the projected image, $y_{project}$ represents a vertical component of the pixel coordinate of the pixel in the projected image, $\theta$ represents the polar angle in the polar coordinate system corresponding to the panoramic image, and $\rho$ represents the radial coordinate in the polar coordinate system corresponding to the panoramic image.

Figure 5:
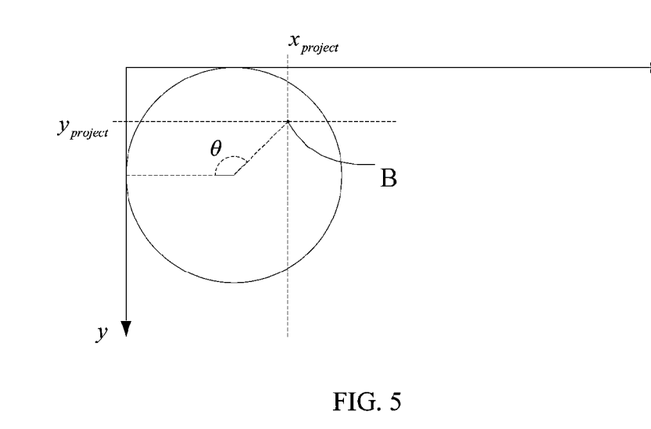
FIG. 5 is a schematic diagram illustrating the coordinate transformation of mapping the panoramic image onto a polar coordinate system to obtain a projected image according to one embodiment of the present disclosure.

For example, referring to FIG. 3, FIG. 4 and FIG. 5, a pixel B ($x_{project}$, $y_{project}$) in the projected image is corresponding to a pixel A ($x_{Panorama}$, $y_{Panorama}$) in the panoramic image, and they both have the same pixel value.

Figure 6:
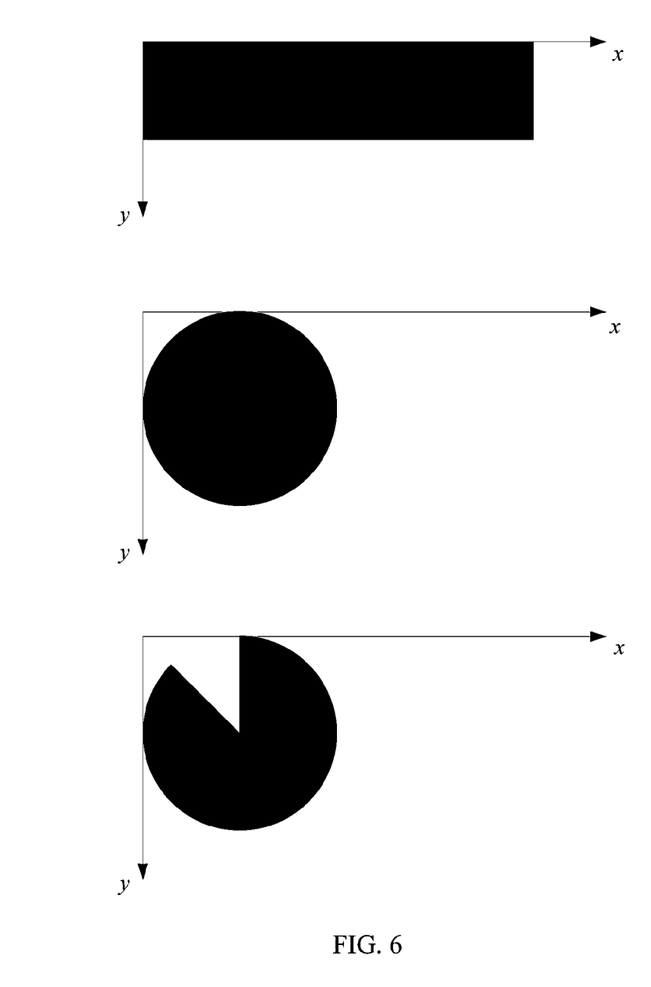
FIG. 6 is a schematic diagram illustrating projected images mapped from the panoramic image based on different panoramic angles according to one embodiment of the present disclosure.

In one embodiment of the present disclosure, if the panoramic angle ratio a is not 1, that is, the panoramic angle of the panoramic image is less than 360 degree, then the projected image obtained is sectorial. For example, referring to FIG. 6, the circular projected image is corresponding to that when the panoramic angle is 360 degree, and the sectorial projected image is corresponding to when the panoramic angle is less than 360 degree.

Figure 7:
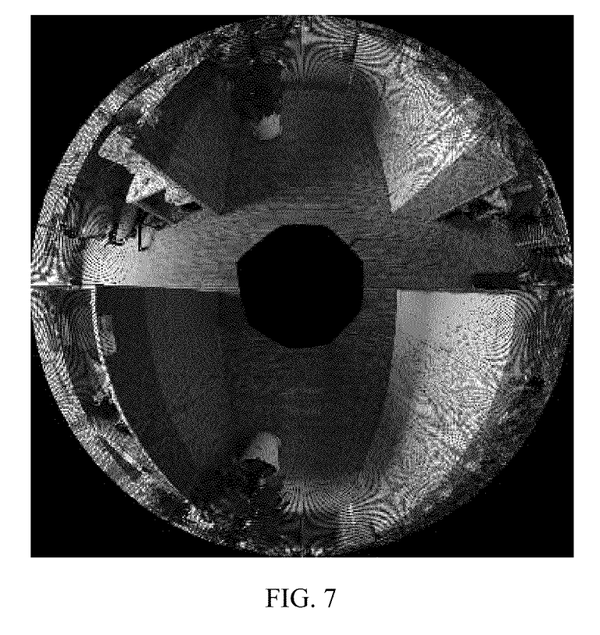
FIG. 7 is an explanatory image illustrating a projected image obtained by mapping the panoramic image to be completed to a polar coordinate system according to one embodiment of the present disclosure.

In one embodiment of the present disclosure, referring to FIG. 2 and FIG. 7, the explanatory projected image in FIG. 7 is obtained by mapping the pixels in FIG. 2 onto the polar coordinate system.

It should be noted that the pixel coordinate or the polar coordinate system calculated by the above projected pixel formula may include an offset, the offset of the pixel coordinate can be offset by translating the whole panoramic image, and the offset of the polar coordinate system can be offset by rotating or scaling, so the offset does not affect the implementation of the whole solution.

In one embodiment of the present disclosure, the coordinate of user input pixel region can be obtained, and the incomplete region can be located based on the input pixel region. For example, the user can select the location of the incomplete region by a cursor box.

In one embodiment of the present disclosure, the step of obtaining a completed image by completing the incomplete region may include:
acquiring an adjacent search region of the incomplete region based on a preset extending radius; acquiring the number of iterations; searching a matching image block in the adjacent search region according to the number of iterations by image pyramid algorithm; and obtaining a completed image by completing the incomplete region based on the matching image block.

In the embodiment, the extending radius is preferably 2 times as big as the radius of the incomplete region.

Furthermore, before the step of obtaining a completed image by completing the incomplete region, it may further include a step of acquiring the resolution of the panoramic image.

In one embodiment, the step of acquiring the number of iterations may include: acquiring the number of iterations corresponding to the resolution of the panoramic image.

For an image with high resolution, if the number of iterations is large, the image pyramid algorithm needs to perform multiple searches in the adjacent search region, which requires a large amount of calculation, causing a slow processing speed. For an image with low resolution, if the number of iterations is less, the number of searches performed by the image pyramid algorithm in the adjacent search region is less, causing a low degree of restoration of the completed image. Therefore, adjusting the number of iterations based on the resolution of the image can ensure the processing speed meeting the real time requirement while ensure the degree of restoration of the completion.

Figure 8:
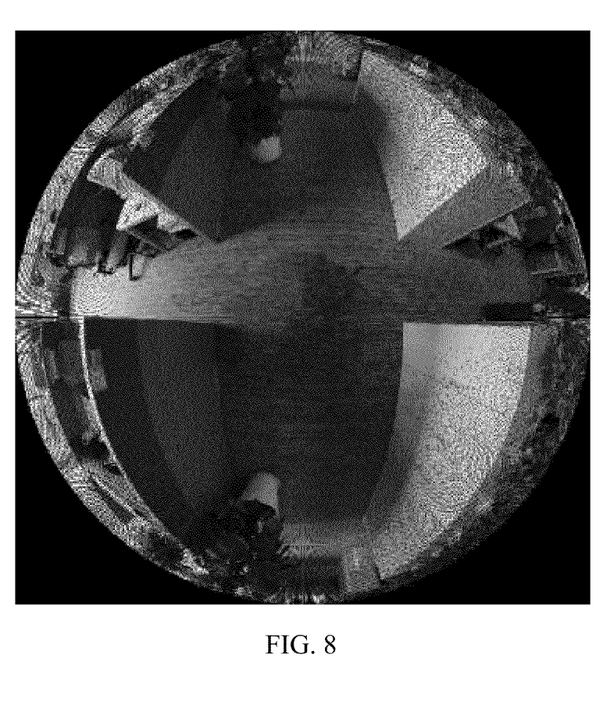
FIG. 8 is an explanatory image illustrating a completed image obtained by completing the projected image according to one embodiment of the present disclosure.

For example, referring to FIG. 7 and FIG. 8, the shaded area in FIG. 7 is the input incomplete region, and FIG. 8 is an explanatory image created by completing the incomplete region by image pyramid algorithm.

Step S108, obtaining a completed panoramic image by inverse mapping the pixels of the completed image according to the polar coordinate system.

The inverse mapping of the completed image is operated in reverse according to the method in Step S104 that mapping the panoramic image to a projected image, so as to obtain a completed panoramic image.

In the embodiment, $x_{Panorama}$ and $y_{Panorama}$ of the completed panoramic image can be obtained based on the inverse operation of the above formula and $x_{project}$ and $y_{project}$ of the pixel in the completed image.

Figure 9:
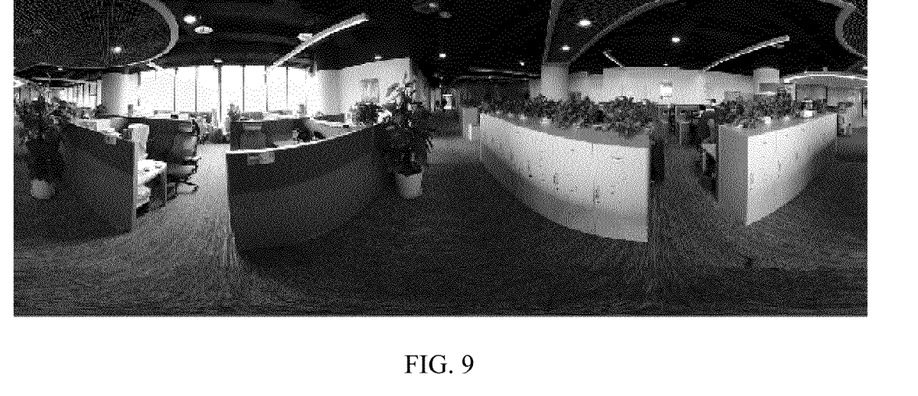
FIG. 9 is an explanatory image illustrating a completed panoramic image obtained by inverse mapping the completed image according to one embodiment of the present disclosure.

For example, referring to FIG. 8 and FIG. 9, FIG. 9 is an explanatory image of the completed panoramic image obtained by the inversion of FIG. 8 in the above formula. It can be seen from FIG. 9 that the incomplete region in the panoramic image has been completed and has a high degree of restoration.

Figure 10:
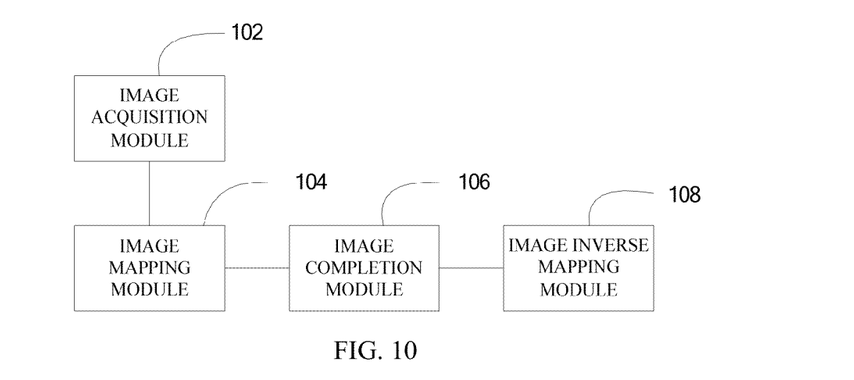
FIG. 10 is a schematic diagram illustrating a device for panoramic image completion according to one embodiment of the present disclosure.

In one embodiment of the present disclosure, as shown in FIG. 10, a device for panoramic image completion includes an image acquisition module 102, an image mapping module 104, an image completion module 106 and an image inverse mapping module 108, wherein the image acquisition module 102 is configured to acquire a panoramic image.

A panoramic image can be an image taken by a panoramic camera. The lens of the panoramic camera is usually a fisheye lens which is an ultra wide-angle spherical lens, rather than a flat lens used by an ordinary camera. As shown in FIG. 2, the panoramic angle of the panoramic image can be 360 degree, that is, an image created by making a complete cycle around a photographer.

The image mapping module 104 is configured to obtain a projected image by mapping pixels of the panoramic image onto a polar coordinate system, wherein the long side component of the pixel coordinate of the pixels is corresponding to the polar angle of the polar coordinate system, and the short side component of the pixel coordinate of the pixels is corresponding to the radial coordinate of the polar coordinate system.

The long side component of the pixel coordinate of the pixels in the panoramic image is a component in the direction extending along the longer edge in the panoramic image, and the short side component of the pixel coordinate of the pixels in the panoramic image is a component in the direction extending along the shorter edge in the panoramic image, referring to FIG. 3.

It should be noted that a longitudinal panoramic image that is shown by longitudinal wide-angle in the visual orientation can be rotate 90 degree to be a transverse panoramic image before mapping.

In other words, by mapping the pixel in the panoramic image onto a polar coordinate system, obtaining the degree of the polar angle corresponding to the pixel in the polar coordinate system based on the long side component of the pixel, and obtaining the length of the radial coordinate corresponding to the pixel in the polar coordinate system based on the short side component of the pixel, a circular or sectorial (circular, when the panoramic angle is 360 degree) projected image can be finally obtained.

In one embodiment of the present disclosure, the image mapping module 104 is configured to calculate the corresponding polar angle based on the long side component of the pixel coordinate of the pixel in the panoramic image, and calculate the corresponding radial coordinate based on the short side component of the pixel coordinate of the pixel in the panoramic image; acquire a projected pixel coordinate of the pixel in the projected image corresponding to the pixel in the panoramic image, to create a projected image.

In the embodiment, the image mapping module 104 can calculate the polar angle and radial coordinate according to a formula of:

$$\begin{cases} \theta = 2\pi \times \frac{x_{Panorama}}{a \times \text{Width}} \\ \rho = b \times (\text{Height} - y_{Panorama}) \end{cases}$$

wherein $x_{Panorama}$ represents the long side component of the pixel coordinate of the pixel in the panoramic image, $y_{Panorama}$ represents the short side component of the pixel coordinate of the pixel in the panoramic image, θ represents the polar angle in the polar coordinate system corresponding to the panoramic image, ρ represents the radial coordinate in the polar coordinate system corresponding to the panoramic image, Width represents the length of the long side of the panoramic image, Height represents the length of the short side of the panoramic image, a represents a panoramic angle ratio, and b represents a scale ratio.

For example, as shown in FIG. 3 and FIG. 4, the panoramic angle ratio a is 1, namely, the panoramic angle of the panoramic image is 360 degree, and the scale ratio b is 1, namely, the maximum length of the radial coordinate is Height.

In the embodiment, the image mapping module 104 can calculate the pixel coordinate of the pixel in the projected image by:

$$\begin{cases} x_{project} = \rho \times (1 + \cos\theta) \\ y_{project} = \rho \times (1 - \sin\theta) \end{cases}$$

wherein $x_{project}$ represents the horizontal component of the pixel coordinate of the pixel in the projected image, $y_{project}$ represents the vertical component of the pixel coordinate of the pixel in the projected image, θ represents the polar angle in the polar coordinate system corresponding to the panoramic image, and ρ represents the radial coordinate in the polar coordinate system corresponding to the panoramic image.

For example, refer to FIG. 3, FIG. 4 and FIG. 5, a pixel B ($x_{project}$, $y_{project}$) in the projected image corresponds to a pixel A ($x_{Panorama}$, $y_{Panorama}$) in the panoramic image, and they both have the same pixel value.

In one embodiment of the present disclosure, if the panoramic angle ratio a is not 1, that is, the panoramic angle of the panoramic image is less than 360 degree, then the projected image obtained is sectorial. For example, referring to FIG. 6, the circular projected image is corresponding to that when the panoramic angle is 360 degree and the sectorial projected image is corresponding to that when the panoramic angle is less than 360 degree.

In one embodiment of the present disclosure, referring to FIG. 2 and FIG. 7, the explanatory projected image by mapping the pixels in FIG. 2 to the polar coordinate system is shown in FIG. 7.

It should be noted that the pixel coordinate or the polar coordinate system calculated by the image mapping module 104 based on the above projected pixel formula can include an offset, the offset of the pixel coordinate can be offset by translating the whole panoramic image, and the offset of the polar coordinate system can be offset by rotating or scaling, thus the offset does not affect the implementation of the whole solution.

The image completion module 106 is configured to acquire an incomplete region of the projected image and obtain a completed image by completing the incomplete region.

In one embodiment of the present disclosure, the image completion module 106 can be used to acquire the coordinate of user input pixel region and locate the incomplete region based on the input pixel region. For example, the user can select the location of the incomplete region by a cursor box.

In one embodiment of the present disclosure, the image completion module 106 can be configured to acquire an adjacent search region of the incomplete region based on a preset extending radius, acquire iterations, search a matching image block in the adjacent search region according to the number of iterations by image pyramid algorithm, and obtain a completed image by completing the incomplete region based on the matching image block.

In the embodiment, the extending radius is preferably 2 times as big as the radius of the incomplete region.

Furthermore, the image completion module 106 can further configured to acquire the resolution of the panoramic image.

In the embodiment, the image completion module 106 can further configured to acquire the number of iterations corresponding to the resolution of the panoramic image.

For an image with high resolution, if the number of iterations is large, the image pyramid algorithm needs to perform multiple searches in the adjacent search region, which requires a large amount of calculation, causing a slow processing speed. For an image with low resolution, if the number of iterations is less, the number of searches performed by the image pyramid algorithm in the adjacent search region is less, causing a low degree of restoration of the completed image. Therefore, adjusting the number of iterations based on the resolution of the image can ensure the processing speed meeting the real time requirement while ensure the degree of restoration of the completion.

For example, referring to FIG. 7 and FIG. 8, the shaded area in FIG. 7 is the input incomplete region (pixel loss region), and FIG. 8 is an explanatory image created by completing the incomplete region by image pyramid algorithm.

The image inverse mapping module 108 is configured to obtain a completed panoramic image by inverse mapping the pixels of the completed image according to the polar coordinate system.

Inverse mapping the completed image is operated in reverse based on the method defined in the image mapping module 104 that mapping the panoramic image to a projected image, so as to obtain a completed panoramic image.

In the embodiment, the image mapping module 104 can be configured to obtain $x_{Panorama}$ and $y_{Panorama}$ of the completed panoramic image based on the inverse operation of the above formula and $x_{project}$ and $y_{project}$ of the pixel in the completed image.

For example, referring to FIG. 8 and FIG. 9, FIG. 9 is an explanatory image of the completed panoramic image obtained by the inversion of FIG. 8 in the above formula. It can be seen from FIG. 9 that the incomplete region in the panoramic image has been completed and has a high degree of restoration.

The above method and device for panoramic image completion firstly map pixels of the panoramic image onto a polar coordinate system to obtain a projected image, then complete the projected image to obtain a completed image, finally inverse map the completed image to obtain a completed panoramic image. Because the angle of a panoramic image has a spherical curvature during photographing or generation, the method that obtaining a projected image by mapping pixels of the panoramic image onto a polar coordinate system then completing the projected image adequately takes account of the perspective curvature of the panoramic image, which avoids serious distortion and stretching not occurring in the completed panoramic image, so as to improve the degree of restoration.

It should be understood for a person skilled in the art that partial or full process to realize the methods in the above embodiments can be accomplished by related hardware (such as terminals) instructed by a computer program, the program can be stored in a computer readable storage medium and the program can include the process of the embodiments of the above methods. Wherein, the storage medium can be a disk, a light disk, a Read-Only Memory or a Random Access Memory. The terminal, as used herein, may refer to any appropriate user terminal with certain computing capabilities, such as a personal computer (PC), a work station computer, a hand-held computing device (tablet), a mobile terminal (a mobile phone or a smart phone), a smart terminal, or any other user-side computing device.

The embodiments are chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A method for panoramic image completion comprising:
   acquiring a panoramic image;
   obtaining a projected image by mapping each pixel coordinate of the panoramic image onto a polar coordinate system, wherein a long side component of the pixel coordinate corresponds to a polar angle of the polar coordinate system and a short side component of the pixel coordinate corresponds to a radial coordinate of the polar coordinate system;
   acquiring an incomplete region of the projected image;
   obtaining a completed image by completing the incomplete region; and
   obtaining a completed panoramic image by inverse mapping each pixel coordinate of the completed image according to the polar coordinate system.

2. The method of claim 1, wherein the obtaining the projected image by mapping each pixel coordinate of the panoramic image onto the polar coordinate system comprises:
   calculating the polar angle based on the long side component of the pixel coordinate in the panoramic image;
   calculating the radial coordinate based on the short side component of the pixel coordinate in the panoramic image; and
   creating a projected image by acquiring a projected pixel coordinate of the projected image corresponding to the pixel coordinate in the panoramic image, based on the polar angle and the radial coordinate.

3. The method of claim 2, wherein the calculating the polar angle based on the long side component of the pixel coordinate in the panoramic image, and the calculating the radial coordinate based on the short side component of the pixel coordinate in the panoramic image comprises:
   calculating the polar angle and the radial coordinate according to a formula of:

$$\begin{cases} \theta = 2\pi \times \frac{x_{Panorama}}{a \times \text{Width}} \\ \rho = b \times (\text{Height} - y_{Panorama}) \end{cases}$$

wherein $x_{Panorama}$ represents the long side component of the pixel coordinate in the panoramic image, $y_{Panorama}$ represents the short side component of the pixel coordinate in the panoramic image, $\theta$ represents the polar angle in the polar coordinate system corresponding to the panoramic image, $\rho$ represents the radial coordinate in the polar coordinate system corresponding to the panoramic image, Width represents the length of the long side of the panoramic image, Height represents the length of the short side of the panoramic image, a represents a panoramic angle ratio, and b represents a scale ratio.

4. The method of claim 2, wherein the creating a projected image by acquiring a projected pixel coordinate of the projected image corresponding to the pixel coordinate in the panoramic image, based on the polar angle and the radial coordinate, comprises:
   calculating the pixel coordinate of the projected image according to a formula of:

$$\begin{cases} x_{project} = \rho \times (1 + \cos\theta) \\ y_{project} = \rho \times (1 - \sin\theta) \end{cases}$$

wherein $x_{project}$ represents a horizontal component of the pixel coordinate of the projected image, $y_{project}$ represents a vertical component of the pixel coordinate of the projected image, $\theta$ represents the polar angle in the polar coordinate system corresponding to the panoramic image and $\rho$ represents the radial coordinate in the polar coordinate system corresponding to the panoramic image.

5. The method of claim 1, wherein the obtaining a completed image by completing the incomplete region comprises:
   acquiring an adjacent search region of the incomplete region based on a preset extending radius;
   acquiring a number of iterations;
   searching a matching image block in the adjacent search region according to the number of iterations by image pyramid algorithm; and
   obtaining a completed image by completing the incomplete region based on the matching image block.

6. The method of claim 5, wherein before the obtaining a completed image by completing the incomplete region, the method further comprises:
   acquiring a resolution of the panoramic image,
   wherein acquiring the resolution of the panoramic image comprises acquiring a number of iterations corresponding to the resolution of the panoramic image.

7. A device for panoramic image completion comprising:
   an image acquisition processor, configured to acquire a panoramic image;
   an image mapping processor, configured to obtain a projected image by mapping pixels of the panoramic image onto a polar coordinate system, wherein a long side component of each pixel coordinate corresponds to a polar angle of the polar coordinate system and a short side component of the pixel coordinate corresponds to a radial coordinate of the polar coordinate system;

an image completion processor, configured to acquire an incomplete region of the projected image and obtain a completed image by completing the incomplete region; and an image inverse mapping processor, configured to obtain a completed panoramic image by inverse mapping each pixel coordinate of the completed image according to the polar coordinate system.

8. The device of claim 7, wherein the image mapping processor is configured to:

calculate the polar angle based on the long side component of the pixel coordinate in the panoramic image;

calculate the radial coordinate based on the short side component of the pixel coordinate in the panoramic image; and generate the projected image by acquiring a projected pixel coordinate of the projected image corresponding to the pixel coordinate in the panoramic image, based on the polar angle and the radial coordinate.

9. The device of claim 8, wherein the image mapping processor is further configured to calculate the polar angle and the radial coordinate according to a formula of:

$$\begin{cases} \theta = 2\pi \times \frac{x_{Panorama}}{a \times \text{Width}} \\ \rho = b \times (\text{Height} - y_{Panorama}) \end{cases}$$

wherein $x_{Panorama}$ represents the long side component of the pixel coordinate in the panoramic image, $y_{Panorama}$ represents the short side component of the pixel coordinate in the panoramic image, $\theta$ represents the polar angle in the polar coordinate system corresponding to the panoramic image, $\rho$ represents the radial coordinate in the polar coordinate system corresponding to the panoramic image, Width represents the length of the long side of the panoramic image, Height represents the length of the short side of the panoramic image, a represents a panoramic angle ratio, and b represents a scale ratio.

10. The device of claim 8, wherein the image mapping processor is further configured to calculate the pixel coordinate in the projected image according to a formula of:

$$\begin{cases} x_{project} = \rho \times (1 + \cos\theta) \\ y_{project} = \rho \times (1 - \sin\theta) \end{cases}$$

wherein $x_{project}$ represents a horizontal component of the pixel coordinate of the projected image, $y_{project}$ represents a vertical component of the pixel coordinate of the projected image, $\theta$ represents the polar angle in the polar coordinate system corresponding to the panoramic image and $\rho$ represents the radial coordinate in the polar coordinate system corresponding to the panoramic image.

11. The device of claim 7, wherein the image completion processor is configured to:

acquire an adjacent search region of the incomplete region based on a preset extending radius;

acquire a number of iterations, search a matching image block in the adjacent search region by the number of iterations by image pyramid algorithm; and obtain a completed image by completing the incomplete region based on the matching image block.

12. The device of claim 11, wherein the image completion processor is configured to acquire a resolution of the panoramic image, and acquire a number of iterations corresponding to the resolution of the panoramic image.

13. A non-transitory computer-readable storage medium comprising an executable program to execute a method for panoramic image completion, the method comprising:

acquiring a panoramic image;

obtaining a projected image by mapping each pixel coordinate of the panoramic image onto a polar coordinate system, wherein a long side component of the pixel coordinate corresponds to a polar angle of the polar coordinate system and a short side component of the pixel coordinate corresponds to a radial coordinate of the polar coordinate system;

acquiring an incomplete region of the projected image;

obtaining a completed image by completing the incomplete region; and obtaining a completed panoramic image by inverse mapping each pixel coordinate of the completed image according to the polar coordinate system.

14. The non-transitory computer-readable storage medium of claim 13, wherein the obtaining a projected image by mapping each pixel coordinate of the panoramic image onto the polar coordinate system comprises:

calculating the polar angle based on the long side component of the pixel coordinate in the panoramic image;

calculating the radial coordinate based on the short side component of the pixel coordinate in the panoramic image; and creating a projected image by acquiring a projected pixel coordinate of the projected image corresponding to the pixel coordinate in the panoramic image, based on the polar angle and the radial coordinate.

15. The non-transitory computer-readable storage medium of claim 14, wherein the calculating the polar angle based on the long side component of the pixel coordinate in the panoramic image, and the calculating the radial coordinate based on the short side component of the pixel coordinate in the panoramic image comprises:

calculating the polar angle and the radial coordinate according to a formula of:

$$\begin{cases} \theta = 2\pi \times \frac{x_{Panorama}}{a \times \text{Width}} \\ \rho = b \times (\text{Height} - y_{Panorama}) \end{cases}$$

wherein $x_{Panorama}$ represents the long side component of the pixel coordinate in the panoramic image, $y_{Panorama}$ represents the short side component of the pixel coordinate in the panoramic image, $\theta$ represents the polar angle in the polar coordinate system corresponding to the panoramic image, $\rho$ represents the radial coordinate in the polar coordinate system corresponding to the panoramic image, Width represents the length of the long side of the panoramic image, Height represents the length of the short side of the panoramic image, a represents a panoramic angle ratio, and b represents a scale ratio.

16. The non-transitory computer-readable storage medium of claim 14, wherein the creating a projected image by acquiring a projected pixel coordinate of the projected image corresponding to the pixel coordinate in the panoramic image, based on the polar angle and the radial coordinate, comprises:

calculating the pixel coordinate of the projected image according to a formula of:

$$\begin{cases} x_{project} = \rho \times (1 + \cos\theta) \\ y_{project} = \rho \times (1 - \sin\theta) \end{cases}$$

wherein $x_{project}$ represents a horizontal component of the pixel coordinate of the projected image, $y_{project}$ represents a vertical component of the pixel coordinate of the projected image, θ represents the polar angle in the polar coordinate system corresponding to the panoramic image and ρ represents the radial coordinate in the polar coordinate system corresponding to the panoramic image.

17. The non-transitory computer-readable storage medium of claim 13, wherein the obtaining a completed image by completing the incomplete region comprises:

acquiring an adjacent search region of the incomplete region based on a preset extending radius;

acquiring a number of iterations;

searching a matching image block in the adjacent search region according to the number of iterations by image pyramid algorithm; and obtaining a completed image by completing the incomplete region based on the matching image block.

18. The non-transitory computer-readable storage medium of claim 17, wherein before the obtaining a completed image by completing the incomplete region, the method further comprises acquiring resolution of the panoramic image, wherein acquiring the resolution of the panoramic image comprises acquiring a number of iterations corresponding to the resolution of the panoramic image.

\* \* \* \* \*